United States Patent [19]

Kee et al.

[11] Patent Number: 5,369,095
[45] Date of Patent: Nov. 29, 1994

[54] COMPOSITIONS AND METHOD COMPRISING SUBSTITUTED GLYCOSIDES AS MUCUS MEMBRANE PERMEATION ENHANCERS

[75] Inventors: Tai-Lee Kee, Grand Prairie, Tex.; Jack M. Shaw, Mechanicsville, Va.

[73] Assignee: Alcon Laboratories, Inc., Fort Worth, Tex.

[21] Appl. No.: 31,000

[22] Filed: Mar. 12, 1993

Related U.S. Application Data

[63] Continuation of Ser. No. 745,136, Aug. 13, 1991, abandoned, which is a continuation-in-part of Ser. No. 480,471, Feb. 14, 1990, abandoned.

[51] Int. Cl.$^5$ .............. A61K 9/10; A61K 31/715; A61K 31/725; A61K 31/79
[52] U.S. Cl. .............................................. 514/24
[58] Field of Search ............. 514/52, 57, 317, 392, 514/402, 915, 960, 946, 947, 777, 781, 772, 780, 779, 772.3, 24, 25, 42, 53; 536/4.1, 23, 53, 54

[56] References Cited

U.S. PATENT DOCUMENTS

| | | | |
|---|---|---|---|
| 4,215,130 | 7/1980 | Sjoerdsma | 514/392 |
| 4,237,141 | 12/1980 | Shiozawa et al. | 514/317 |
| 4,558,063 | 12/1985 | Beeley et al. | 514/402 |
| 4,722,837 | 2/1988 | Cameron | 252/174.17 |
| 4,725,590 | 2/1988 | Ritchey | 514/166 |
| 4,742,083 | 5/1988 | Ritchey | 514/621 |
| 4,921,838 | 5/1990 | Catsimpoolas et al. | 514/25 |
| 4,923,693 | 5/1990 | Michalos | 514/915 |
| 4,942,038 | 7/1990 | Wallach | 424/450 |
| 5,041,450 | 8/1991 | Chiou et al. | 514/915 |
| 5,062,989 | 11/1991 | Kamegai et al. | 252/174.17 |
| 5,219,887 | 6/1993 | Andrews et al. | 514/881 |
| 5,262,178 | 11/1993 | Malfroy Camine et al. | 435/212 |

FOREIGN PATENT DOCUMENTS 1-151528 6/1989 Japan.

OTHER PUBLICATIONS

Tonjum, Asbjorn M., "Permeability of Rabbit Corneal Epithelium in Horseradish Peroxidase After the Influence of Benzalkonium Chloride," *Acta Ophthalmologica*, vol. 53, p. 335 (1975).

Morimoto et al., "Evaluation of permeability enhancement of hydrophilic compounds and macromolecular compounds by bile salts through rabbit corneas in vitro," *J. Pharm. Pharmacol.*, vol. 39, p. 124 (1987).

Schulte, Thomas L., "Ophthalmic compositions containing biphenamine and their use in the treatment or prevention of inflammation," *Chemical Abstracts*, vol. 106, 125931t, p. 402 (1987).

Grass et al., "Mechanisms of Corneal Drug Penetration I. In Vivo and In Vitro Kinetics," *Journal of Pharmaceutical Sciences*, vol. 77, No. 1, p. 3 (Jan., 1988).

Newton et al., "Topically Applied Cyclosporine in Azone Prolongs Corneal Allograft Survival," *Investigative Ophthalmology & Visual Science*, vol. 29, No. 2, p. 208 (Feb., 1988).

*Primary Examiner*—Ronald W. Griffin
*Attorney, Agent, or Firm*—Sally Yeager

[57] ABSTRACT

The use of substituted glycosides to enhance the penetration of drugs across mucus covered epithelial tissues of humans and animals is disclosed, including enhanced penetrations of topically applied ophthalmic drugs through the corneal epithelium of said humans and animals.

10 Claims, 2 Drawing Sheets

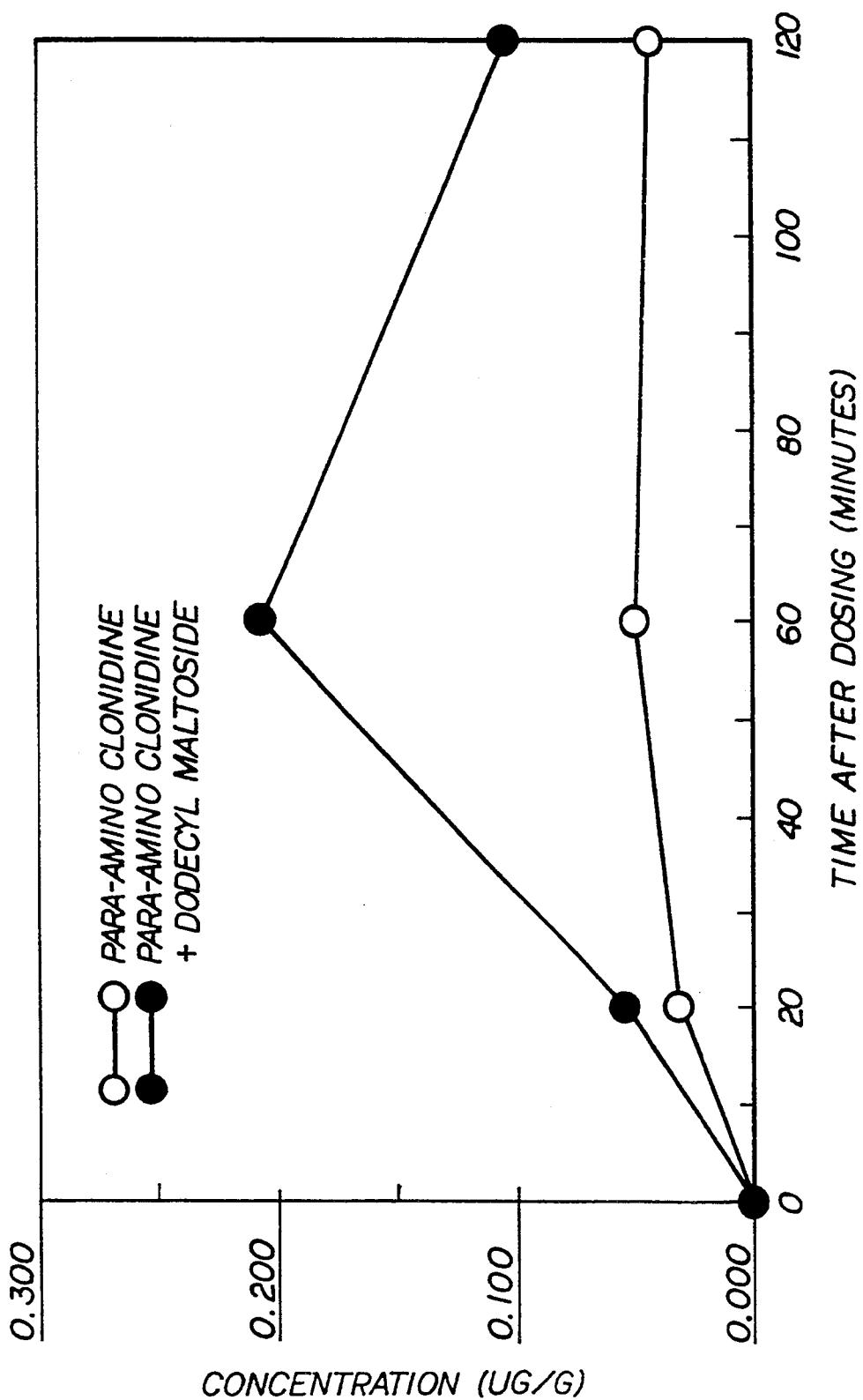

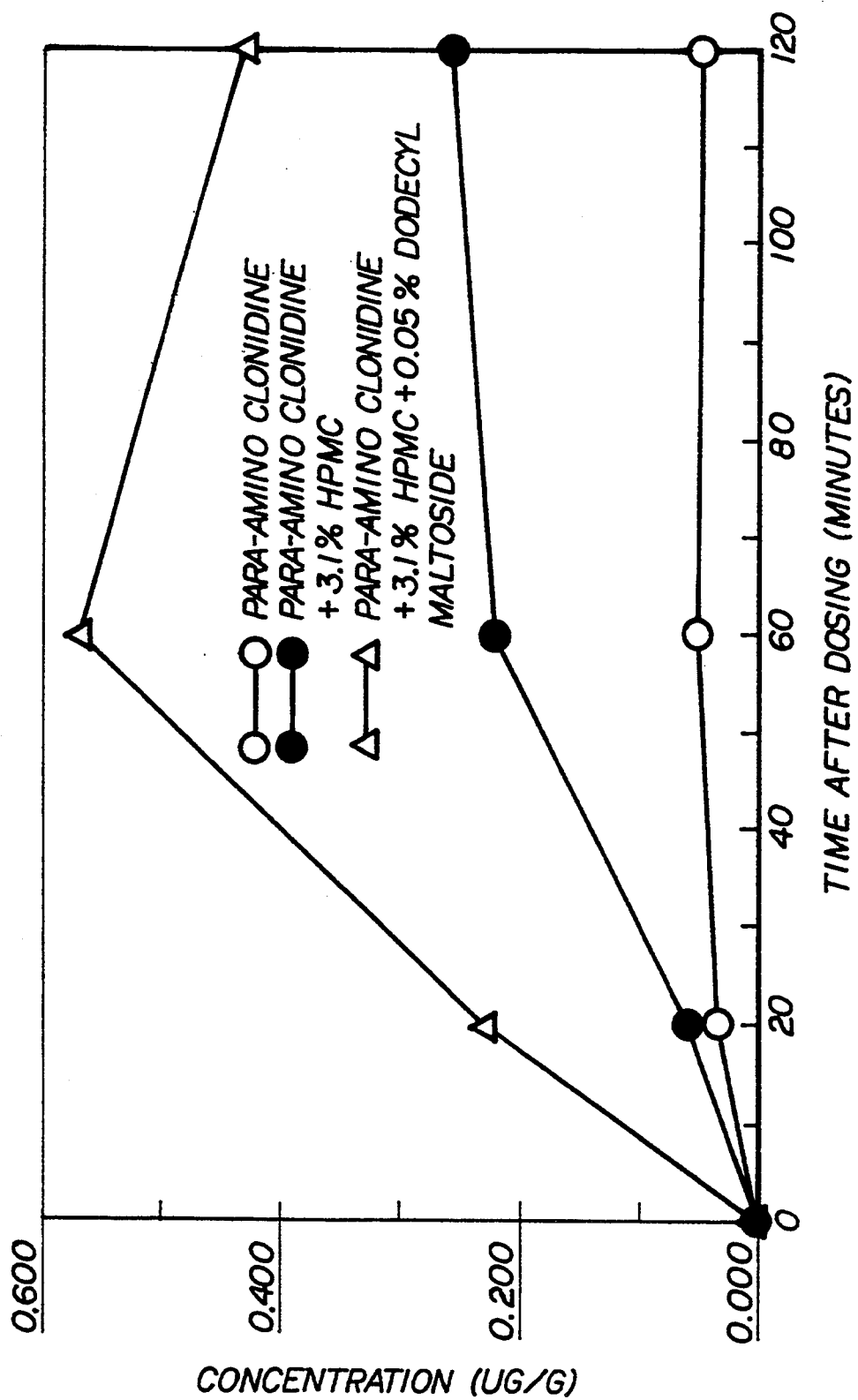
FIG II

COMPOSITIONS AND METHOD COMPRISING SUBSTITUTED GLYCOSIDES AS MUCUS MEMBRANE PERMEATION ENHANCERS

CROSS-REFERENCE TO RELATED APPLICATIONS

This is a continuation of U.S. Ser. No. 07/745,136, filed Aug. 13, 1991 (now abandoned), which is a continuation-in-part of U.S. Ser. No. 07/480,471, filed Feb. 14, 1990 (now abandoned).

FIELD OF THE INVENTION

This invention relates to substituted glycosides as enhancers for the permeation of therapeutic agents through mucus membranes of humans and animals.

BACKGROUND OF THE INVENTION

The present invention relates to the field of drug delivery across mucus covered epithelial tissues of humans and animals. Such tissues include nasal, pulmonary, rectal, buccal, vaginal, uteral, and gastrointestinal routes for drug administration. More particularly, this invention relates to enhancement of the penetration of ophthalmic drugs and other therapeutic agents through the cornea and other tissues of the eye such as the sclera and conjunctiva of humans and animals.

In order for an ophthalmic drug to be therapeutically effective, it is generally necessary for the drug to penetrate the cornea and be taken up in the aqueous humor, ciliary processes and other tissues in the eye. There are notable exceptions to this general rule, such as drugs or drug products which produce a localized therapeutic effect by acting on the exterior surface of the cornea (e.g., drugs or drug products useful in improving ocular comfort and/or treating dry or irritated eyes). However, the treatment of conditions involving physiological mechanisms within the eye (e.g., glaucoma, diabetic retinopathy, cataracts, etc.) generally does require the permeation of topically applied ophthalmic drugs primarily through the cornea.

In order for a drug to pass through the cornea, it must penetrate three layers of tissue, namely, the epithelium, stroma, and the endothelium. Except for highly lipophilic drugs, the epithelium is the main barrier to drug penetration of the cornea. Penetration of the stroma basically involves diffusion of the drug through a barrier which is approximately 360 microns thick. There are currently no known methods of enhancing drug penetration through the stroma or endothelium. However, it is possible to enhance the penetration of drugs through the epithelium, and thereby enhance the overall absorption of drugs applied topically to the eye. The present invention is directed to such enhancement.

There have been prior attempts to enhance the penetration of drugs through the corneal epithelium. The goal of such attempts has generally been to enhance penetration of drugs through the corneal epithelium to an optimal point at which the stroma alone controls drug transport through the corneas. The prior attempts have included use of chemical agents to enhance the penetration of drugs through the epithelium. It has been reported that benzalkonium chloride (BAC), bile salts, dimethyl sulfoxide (DMSO), ethylenediamine tetraacetate (EDTA) and 1-dodecylazayl-cycloheptan-2-one (AZONE®) enhance the corneal penetration of certain drugs. The following publications may be referred to for further background concerning the use of such agents to enhance corneal penetration: *Acta Ophthalmologica*, Vol. 53, p.335 (1975); *J. Pharm. Pharmacol.*, Vol.39, p.124 (1987); *Chem. Abstracts*, Vol.106, 125931t, p.402 (1987); *Journal of Pharmaceutical Sciences*, Vol.77, No.1 (Jan.,1988); and *Investigative Ophthalmology and Visual Science*, Vol.29, No.2 (Feb.,1988). Notwithstanding such prior attempts, there continues to be a need for a means of safely and effectively enhancing the penetration of drugs through the cornea.

SUMMARY OF THE INVENTION

A principal objective of the present invention is to provide for a method of enhancing drug delivery across mucus covered epithelial tissues, particularly those of the cornea, sclera and conjunctiva of humans and animals. A further objective of the present invention is to provide topical ophthalmic compositions containing one or more agents for enhancing the penetration of the active ingredient(s) contained therein.

The foregoing objectives and other general objectives of the present invention are satisfied by the provision of a means of enhancing penetration by using a class of compounds collectively referred to herein as substituted glycosides to enhance the penetration of ophthalmic drugs through the corneal epithelium, sclera and conjunctiva. In addition, the objectives of the present invention are furthered when viscosity enhancing polymers are used in conjunction with the substituted glycosides and ophthalmic drugs so that the compositions are retained in the eye for a relatively longer period of time, thus allowing the enhancers more time to facilitate drug transport through the cornea, sclera and conjunctiva.

BRIEF DESCRIPTION OF THE FIGURES

FIG. I compares the amount of a drug, para-aminoclonidine, found in the aqueous humor of rabbits which were administered, the drug with and without the substituted glycoside enhancer, dodecyl maltoside.

FIG. II compares the amount of a drug, para-aminoclonidine, found in the aqueous humor of rabbits which were administered the drug as a solution, or the drug in combination with a viscosity enhancing polymers, hydroxypropylmethyl cellulose (HPMC) and dodecyl maltoside, or the drug with HPMC.

DETAILED DESCRIPTION OF THE INVENTION

The present invention is based on the discovery that substituted glycosides effectively and safely enhance the corneal penetration of ophthalmic drugs. When "corneal penetration" is used herein it includes penetration through the cornea, sclera and conjunctiva of the eye. These penetration enhancers can be used in compositions comprising any ophthalmic drug which, to be effective, must be substantially taken up by the aqueous humor, ciliary processes and other tissues in the eye upon topical administration. Examples of classes of ophthalmic drugs with which the substituted glycosides of the present invention can be used, include: steroids, growth factors, cycloplegics, miotics, mydriatics, therapeutic proteins and peptides, antioxidants, aldose reductase inhibitors, nonsteroidal antiinflammatories, immunomodulators, antiallergics, antimicrobials, angiostatic agents and anti-glaucoma therapeutic agents.

The penetration enhancing substituted glycosides used in the present invention have the following structure:

wherein $R_1$ is a hydrophobic group including saturated and unsaturated aliphatic hydrocarbon groups which range from 8 to 28 carbons in length with 1 to 5 double bonds. The aliphatic hydrocarbon group can be a straight or branched chain and may be substituted by one or more aromatic, cycloaliphatic or hydrophilic (e.g. hydroxyl, thiol, ester or amino) groups. $R_2$ is a group derived from any cyclic or acyclic saccharide containing 4–7 carbons and their isomers;

X is an integer from 1–10; and

Z is an oxy (—O—), carbonyloxy

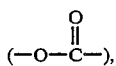

phosphoryl

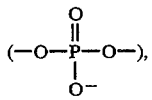

thio (—S—), or
carboxamido

where $R_2$ covalently bound to such group.

More specifically $R_1$ can be a straight 8–18 carbon alkyl chain in hemiacetal linkage (glycoside) to the saccharide; and $R_2$ a group derived from any of a variety of isomeric saccharides containing 5 or 6 carbons. The saccharide can be, for example, an aldehyde-containing saccharide (glucose, mannose, arabinose, galactose, xylose); a ketone-containing saccharide (fructose, xylulose, sorbose); a saccharide alcohol (sorbitol, inositol, xylitol, mannitol); a saccharide acid (glucuronic acid, neuramic acid, mannuronic acid); a deoxysaccharide (deoxy-ribose, rhamnose,); an aminosaccharide (glucosamine, galactosamine). Higher order saccharides being covalently linked in any of a number of ways to form different isomeric structures include for example disaccharides such as maltose, cellobiose, sucrose and lactose and trisaccharides, such as raffinose.

The preferred penetration enhancers are alkyl chain containing glycosidas derived from maltose and glucose with $R_1$ being 8 to 18 carbons and having the following structures:

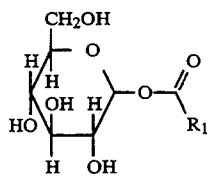

[A]

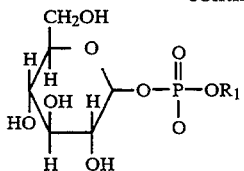

[B]

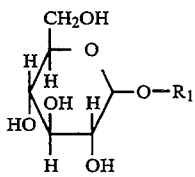

[C]

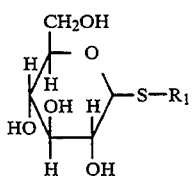

[D]

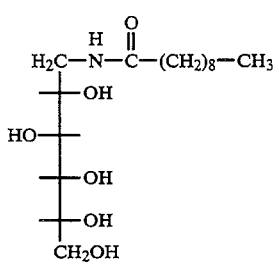

[E]

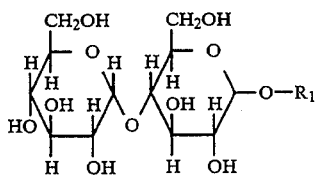

[F]

The most preferred penetration enhancer is:

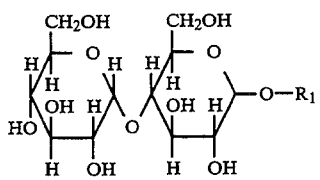

Dodecyl Maltoside

The substituted glycosides which are useful in the present invention may be described as being "amphipathic", since they include both hydrophilic and hydrophobic groups. While not wishing to be bound by any theory, it is believed that substituted glycosides enhance the corneal penetration of drugs by partition and interaction with protein, glycoprotein and lipid components present in the membrane of the corneal epithelium. Such interaction is believed to alter the degree of order of the proteins and lipids in the membrane, thereby modifying the function of the epithelium as a barrier to drug penetration. Whatever the mechanism, the net result is that drug penetration across the epithelium is enhanced.

The use of substituted glycosides in accordance with the present invention to enhance corneal penetration of drugs significantly increases the amount of drug which is able to penetrate the cornea. The degree of enhancement will vary with different drugs, but in some cases may be as much as 3-fold or more. Because drugs can more effectively penetrate the cornea, less drug is lost due to flow down the punctum and therefore less drug need be administered to effectively treat a particular indication. This is particularly beneficial when it is necessary to administer drugs which cause severe systemic side effects.

The amount of substituted glycoside required in order to enhance cornea penetration will depend on various factors, such as the solubility, partition coefficient and molecular weight of the ophthalmic drug or therapeutic agent; the excipients (surfactants, preservatives, viscosity enhancing polymers) present in the formulation; and the particular enhancer being used. In general, the more lipophilic the drug to be delivered, the less enhancer is required to increase penetration, and the higher the concentration of the substituted glycoside, the better the corneal penetration. Typically, one or more enhancers will be used in an amount of from about 0.01% to about 20% (weight/volume) preferably from about 0.01 to 1.0%.

The substituted glycosides can be used with certain topical drug delivery systems wherein an excipient or vehicle will not substantially impair or prevent the substituted glycosides from functioning as corneal penetration enhancers. For example, the substituted glycosides can be formulated in compositions which are solutions, suspensions, ointments, gels or films. The, type of composition will depend on, among other things, the chemical and physical properties of the drug or therapeutic agent to be delivered and the properties of polymeric materials used in the formulation. These properties are well known to a person of ordinary skill in the art of drug formulation and delivery.

In a preferred embodiment, the present invention further comprises the use of viscosity enhancing polymers in conjunction with the substituted glycosides to enhance ocular bioavailability. The longer a topical ophthalmic formulation is in contact with the eye the better the ocular bioavailability. Through the use of polymers in conjunction with the above described enhancers the compositions of the present invention are retained on the cornea longer. As a result, the penetration enhancing components of the compositions can more effectively interact with the corneal epithelium to enhance penetration of the desired drugs or therapeutic agents into the eye. It has been found that the use of polymers in conjunction with substituted glycosides can provide for up to about a 3 to 10 fold increase in the amount of drug or therapeutic agent made available to the tissues. The effectiveness of the therapeutic agent and the substituted glycosides can be improved when the viscosity of the compositions is increased up to about 1000 centipoise (cps), preferably between about 50 cps. to 300 cps. Polymers are added to provide for this desired viscosity increase.

Any synthetic or natural polymer which will increase viscosity and is compatible with tissues of the eye and the ingredients of the substituted glycoside compositions can be used. Such polymers are referred to herein as "viscosity enhancing, ophthalmically acceptable polymers." Examples include, but are not limited to: natural polysaccharides and gums, such as alginates, carrageenans, guar, karaya, locust bean, tragacanth and xanthan; and synthetic polymers, such as carbomer, hydroxyethylcellulose (HEC), hydroxypropylcellulose, hydroxypropylmethylcellulose (HPMC), methylcellulose, polyvinyl alcohol (PVA), polyvinyl pyrrolidone, carboxymethylcellulose and agarose. In addition, proteins, synthetic polypeptides and polymer-peptide copolymers which enhance viscosity and are ophthalmically acceptable can be used to increase the viscosity of the compositions to provide for better bioavailability. Typically, proteins which can be used include: gelatin, collagen, albumin and casein.

The preferred viscosity enhancing agents are one or more polymers selected from: PVA, HPMC and HEC. The most preferred agent is HPMC. The viscosity enhancing agents are added to provide for compositions with a viscosity of between about 50 and 300 cps.

The preferred method for enhancing the penetration of a drug or therapeutic agent comprises the use of dodecyl maltoside at a concentration of about 0.01% to 1.0% in combination with the polymer, HPMC, in an amount sufficient to provide a composition with a viscosity of about 50 to about 300 cps.

The following examples further illustrate the compositions which, according to the present invention, comprise the corneal penetration enhancing properties of the substituted glycosides and their use to enhance cornea penetration.

EXAMPLE 1

The following formulation is an example of a topical ophthalmic composition which can be used to treat glaucoma.

| Ingredients | Formulation % (weight/volume) |
| --- | --- |
| Para-amino-clonidine | 0.125 |
| Dodecyl maltoside | 0.050 |
| Benzalkonium chloride | 0.01 |
| Disodium Edetate, USP | 0.01 |
| Sodium phosphate, monobasic, USP | 0.18 |
| Sodium phosphate, dibasic, USP | 0.12 |
| Mannitol, USP | 3.3 |
| HCl, NF and/or NaOH, NF | q.s. pH to 6.5 ± 0.2 |
| Purified Water, USP | q.s. 100 |

Procedure for Preparation of Formulation

Approximately 85% (8.5 ml) of the batch volume of purified water was added to a container. All of the ingredients were added to the container: 0.018 g monobasic sodium phosphate; 0.012 g dibasic sodium phosphate; 0.33 g mannitol; 0.1 ml of 1.0% BAC; 0.001 g disodium edetate; 0.0125 g para-aminoclonidine. The ingredients were mixed well and stirred until all ingredients dissolved into a solution. 0.005 g dodecyl maltoside was added to the container and sonicated for 5 minutes. The pH was adjusted to pH 6.5. Purified water was then poured through a sterilizing filter into the container (q.s. to 10 ml) and the solution was mixed well.

Nine New Zealand albino rabbits were selected for evaluation of the penetration through the cornea of the para-amino-clonidine formulation set forth above. All rabbits received 30 ul of the 0.125% para-amino-clonidine topically in both eyes. Three rabbits were sacrificed at 20 minutes from dosing and aqueous humor was withdrawn from their eyes. The aqueous humor as assayed by liquid scintillation counting to determine the amount of para-amino-clonidine in the aqueous humor. The same procedure was done on 3 different rabbits at 60 minutes from dosing and on another 3 rabbits, 120 minutes from dosing. Nine control rabbits received 0.125% para-aminoclonidine as set forth in the formulation above without 0.05% dodecyl maltoside. Aqueous humor was withdrawn and assayed as explained above. The results are shown in the graph depicted in FIG. I. It can be seen from the graph that the amount of para-amino-clonidine in the aqueous humor is greater in the rabbits treated with the formulation containing dodecyl maltoside. At 60 minutes there is almost a four fold increase in the amount of para-aminoclonidine found in the aqueous humor of those rabbits which received the drug in conjunction with dodecyl maltoside versus those who received the drug without dodecyl maltoside. Therefore, the results indicate that dodecyl maltoside enhanced penetration of para-aminoclonidine through the cornea.

EXAMPLE 2

| Formulation Ingredients | % (Weight/volume) |
|---|---|
| Para-amino-clonidine | 0.125 |
| Hydroxypropylmethylcellulose-E50LV, (HPMC) USP | 3.1 |
| Dodecyl maltoside | 0.05 |
| Benzalkonium chloride | 0.01 |
| Disodium Edetate, USP | 0.01 |
| Sodium phosphate, monobasic, USP | 0.18 |
| Sodium phosphate, dibasic, USP | 0.12 |
| Mannitol, USP | 3.3 |
| HCl, NF and/or NaOH, NF | q.s. pH to 6.75 ± 0.2 |
| Purified Water, USP | q.s. 100 |

Procedure for Preparation of Formulation

Approximately 85% (8.5 ml) of the batch volume of purified water was added to a container. All of the ingredients were then added to the container: 0.018 g monobasic sodium phosphate; 0.33 g mannitol; 0.1 ml of 1.01% BAC; 0.001 g disodium edetate; 0.0125 g para-amino-clonidine; 0.31 g HPMC. The ingredients were mixed well. 0.005 g dodecyl maltoside was added to the container and sonicated 5 minutes. The pH was adjusted to pH 6.5. Purified water was then poured through a sterilizing filter into the container (q.s. to 10 ml) and the solution was mixed well.

Nine New Zealand albino rabbits were selected for evaluation of the penetration through the cornea of the para-amino-clonidine formulation set forth above. All rabbits received 30 ul of the 0.125% para-amino-clonidine topically in both eyes. Three rabbits were sacrificed at 20 minutes from dosing and their aqueous humor was withdrawn from their eyes. The aqueous humor was assayed by liquid scintillation counting to determine the amount of para-amino-clonidine in the aqueous humor. The same procedure was done on three different rabbits at 60 minutes from dosing and on another three rabbits, 120 minutes from dosing. Nine control rabbits received 0.125% para-amino-clonidine as set forth in the formulation above without 0.05% dodecyl maltoside and 3.1% HPMC. Another 9 rabbits received 0.125% para-aminoclonidine as set forth in the formulation above without 0.05% dodecyl maltoside. Aqueous humor was withdrawn and assayed as explained above. The results are shown in the graph depicted in FIG. II. It can be seen from the graph that the amount of para-amino-clonidine in the aqueous humor is greater in the rabbits treated with the formulation containing HPMC and HPMC with dodecyl maltoside. At 60 minutes there is almost a 4.0 fold and a 10 fold increase in the amount of para-aminoclonidine found in the aqueous humor of those rabbits which received the drug in conjunction with HPMC or with HPMC and dodecyl maltoside, respectively, as compared to those which received the drug without HPMC or HPMC and dodecyl maltoside. The results indicate that dodecyl maltoside enhances the penetration of para-amino-clonidine through the cornea over HPMC alone and para-aminoclonidine alone.

EXAMPLE 3

The following carbachol formulations were prepared and evaluated for Acute Pupil Diameter Response in New Zealand Albino Rabbits. Animals were restrained for the duration of a study. For 30 minutes animals were adapted to room lighting and then the eyelashes were trimmed. Two baseline pupil diameter measurements were taken with a hand-held micrometer on one eye of each animal. This eye was then dosed with one 30 microliter aliquot of each formulation and subsequent pupil diameter measurements taken at 0.5, 1, 2, 3, 4, and 5 hours. The results are shown in Table 1.

| Formulation Compound | A wt. % | B wt. % | C wt. % |
|---|---|---|---|
| $NaH_2PO_4$ | 0.18 | 0.18 | 0.18 |
| $Na_2HPO_4$ | 0.12 | 0.12 | 0.12 |
| EDTA | 0.01 | 0.01 | 0.01 |
| BAC | 0.01 | 0.01 | 0.01 |
| Carbachol | 0.3 | 0.3 | 3 |
| Dodecyl Maltoside | 0 | 0.07 | 0 |
| HPMC | 0 | 3.3 | 0 |
| Water | q.s. to 100 | q.s. to 100 | q.s. to 100 |
| pH was adjusted to 6.5 | | | |

TABLE 1

MEAN PERCENT CHANGE IN RABBIT PUPIL DIAMETER

| | Time after treatment (hrs.) | | | | | |
|---|---|---|---|---|---|---|
| Formulation | 0 | ½ | 1 | 2 | 3 | 4 | 5 |
| A (0.3% Carbachol) | 0 | −22 | −28 | −20 | −13 | −5 | −1 |
| B (0.3% Carbachol + 0.07 DDM + 3.3% HPMC) | 0 | −63 | −66 | −61 | −56 | −36 | −23 |
| C (3% Carbachol) | 0 | −45 | −44 | −35 | −27 | −15 | −10 |

As evident from the data, Formulation B containing Carbachol with dodecyl maltoside and hydroxypropyl methylcellulose is far superior to control (Formulation A) and to a formulation (Formulation C) with 10 times higher drug concentration. Formulation B is useful for the treatment of glaucoma.

EXAMPLE 4

The procedure in Example 3 was repeated, except Carbachol was substituted with 1% amount by weight of Pilocarpine in Formulations A and B and with 4% Pilocarpine in Formulation C. The results are shown in Table 2.

TABLE 2

MEAN PERCENT CHANGE IN RABBIT PUPIL DIAMETER

| | Time after treatment (hrs.) | | | | | |
|---|---|---|---|---|---|---|
| Formulation | 0 | ½ | 1 | 2 | 3 | 4 | 5 |
| A (1% Pilocarpine) | 0 | −37 | −26 | −15 | −5 | 0 | 0 |
| B (1% Pilocarpine + 0.07% DDM + 3.3% HPMC) | 0 | −45 | −38 | −28 | −17 | −6 | 0 |

TABLE 2-continued

MEAN PERCENT CHANGE IN RABBIT PUPIL DIAMETER

| Formulation | Time after treatment (hrs.) | | | | | |
|---|---|---|---|---|---|---|
| | 0 | ½ | 1 | 2 | 3 | 4 | 5 |
| C (4% Pilocarpine) | 0 | −37 | −34 | −23 | −8 | −5 | −1 |

The results clearly indicate that Pilocarpine Formulation B with the enhancer dodecyl maltoside and a viscosity enhancing agent, HPMC, shows superior permeation to control formulations. Formulation B is useful in the treatment of glaucoma.

EXAMPLE 5

The procedure of Example 3 was repeated, except Carbachol was substituted with 1% amount by weight of Epinephrine in Formulation A and 0.3 and 3% in Formulations B and C respectively. The results are shown in Table 3.

TABLE 3

MEAN PERCENT CHANGE IN RABBIT PUPIL DIAMETER

| Formulation | Time after treatment (hrs.) | | | | | |
|---|---|---|---|---|---|---|
| | 0 | ½ | 1 | 2 | 3 | 4 | 5 |
| A (1% Epinephrine) | 0 | 0 | 0 | 0 | 0 | 0 | 0 |
| B (0.3% Epinephrine + 0.07% DDM + 3.3% HPMC) | 0 | 53 | 63 | 60 | 50 | 40 | 28 |
| C (3% Epinephrine) | 0 | 22 | 22 | 15 | 10 | 10 | 6 |

From the data it is evident that Formulation B with the enhancer dodecyl maltoside and viscosity enhancing agent HPMC permeates far better through the cornea than Formulation C with 10 fold higher drug concentration. Formulation B is useful in the treatment of glaucoma.

EXAMPLE 6

The procedure of Example 3 was repeated, except Carbachol was substituted with 0.25% amount by weight of Phenylephrine in Formulations A and B and 2.5% in Formulation C. The results are shown in Table 4.

TABLE 4

MEAN PERCENT CHANGE IN RABBIT PUPIL DIAMETER

| Formulation | Time after treatment (hrs.) | | | | | |
|---|---|---|---|---|---|---|
| | 0 | ½ | 1 | 2 | 3 | 4 | 5 |
| A (0.25% Phenylephrine) | 0 | 5 | 9 | 0 | 0 | 0 | 0 |
| B (0.25 Phenylephrine + 0.07% DDM + 3.3% HPMC) | 0 | 53 | 55 | 41 | 25 | 9 | 3 |
| C (2.5% Phenylephrine) | 0 | 30 | 36 | 26 | 20 | 10 | 7 |

The results show that Formulation B, useful in the treatment of glaucoma, is far superior even at 1/10th concentration when formulated with enhancer dodecyl maltoside and the viscosity enhancing agent, HPMC, and shows higher permeation through corneal epithelium than control.

EXAMPLE 7

The following Ciprofloxacin formulations were prepared and their permeation through rabbit cornea was evaluated by measuring the concentration in aqueous humor according to the procedure described in Example 2. The results are shown in Table 5.

| | Formulation A (wt. %) | Formulation (B (wt. %) |
|---|---|---|
| Na Acetate Trihydrate | 0.03 | 0.03 |
| Acetic Acid 6N | 0.0043 to pH 4.5 | 0.0043 to pH 4.5 |
| Mannitol | 4.6 | 4.6 |
| BAC | 0.01 | 0.01 |
| EDTA | 0.05 | 0.05 |
| Ciprofloxacin | 0.30 | 0.30 |
| Dodecyl Maltoside | 0.00 | 0.07 |
| HPMC | 0.00 | 3.30 |
| Water | q.s. to 100 | q.s. to 100 |

TABLE 5

Aqueous Humor Concentration of Ciprofloxacin (ng/ml)

| | 30 min. | 60 min. | 120 min. |
|---|---|---|---|
| Formulation A | 13.99 | 24.10 | 34.37 |
| Formulation B | 108.78 | 250.77 | 394.95 |

It can be seen that Formulation B containing Ciprofloxacin, the enhancer dodecyl maltoside and viscosity enhancing agent HPMC is 10 times more permeable through the cornea as compared to control formulation A. Formulation B is useful in the treatment of bacterial conjunctivitis and corneal ulcers.

EXAMPLE 8

Albino rabbits were sacrificed, and within 15 minutes, the corneas were mounted and clamped between diffusion cells according to the published procedure by Schoenwald et al. (J. Pharm. Sci. 72, 1266, 1983). 7 ml of bicarbonated Ringer's solution containing reduced glutathione was added to the endothelial side to serve as the receiver solution. An equal volume of the same solution containing Atenolol, a β-blocker, with or without dodecyl maltoside (DDM) was added to the epithelial side to serve as the donor solution. The apparent permeability coefficient was calculated from the average cumulative amount of drug penetrating through the cornea over time according to Schoenwald.

The following solution formulations were used.

| | A (Control) (wt. %) | B (wt. %) | C (wt. %) |
|---|---|---|---|
| NACl | 0.652 | 0.652 | 0.652 |
| KCl | 0.0359 | 0.0359 | 0.0359 |
| $CaCl_2.2H_2O$ | 0.0153 | 0.0153 | 0.0153 |
| $MgCl_2.6H_2O$ | 0.0159 | 0.0159 | 0.0159 |
| $NaH_2PO_4$ | 0.0103 | 0.0103 | 0.0103 |
| $NaHCO_3$ | 0.2453 | 0.2453 | 0.2453 |
| Glucose | 0.0903 | 0.0903 | 0.0903 |
| Reduced Glutathione | 0.0092 | 0.0092 | 0.0092 |
| Atenolol | 0.03 | 0.03 | 0.03 |
| Dodecyl Maltoside | 0 | 0.01 | 0.10 |
| Water q.s. | 100 | 100 | 100 |

| Permeability Coefficient (cm/sec × $10^{-6}$) | |
|---|---|
| Formulation A | 2.3 |
| B | 17.3 |
| C | 50.8 |

The results clearly indicate that the formulations containing 0.01 and 0.1% of dodecyl maltoside showed superior permeation (7.5 and 22.1) fold respectively) for Atenolol as compared to control.

EXAMPLE 9

The procedure in Example 8 was repeated with the following para-amino clonidine formulations.

| Formulation | permeability coefficient (cm/sec × $10^{31\,6}$) |
|---|---|
| 05% para-amino clonidine | 3.8 |
| 05% para-amino clonidine + 0.01% DDM | 22.0 |
| 05% para-amino clonidine + 0.1% DDM | 39.0 |

The results clearly indicate that the formulations containing dodecyl maltoside showed superior permeation for para-amino clonidine as compared to control.

EXAMPLE 10

The procedure of Example 8 was repeated with Atenolol except dodecyl maltoside was substituted with 0.1% amount by weight of each of the following substituted glycosides of this invention and the following results were obtained.

| Enhancer | Permeability Coefficient (cm/sec × $10^{-6}$) |
|---|---|
| Tetradecyl maltoside | 16.8 |
| Decyl maltoside | 26.7 |
| Nonyl β-D-glucoside | 14.7 |
| Decyl β-D-glucoside | 49.21 |
| Undecyl β-D-glucoside | 25.3 |
| Dodecyl β-D-glucoside | 15.6 |
| Octyl thioglucoside | 9.0 |
| Decanoyl N-methylglucosamide | 26.0 |
| Sucrose monolaurate | 42.8 |
| Lysophosphatidyl Inositol, 0.01% | 14.0 |

The results clearly show that these substituted glycosides increase the corneal permeation of atenolol several fold over control.

EXAMPLE 11

The following anti-allergic formulation was prepared:

| | % w/v |
|---|---|
| Lodoxamide | 0.1 |
| Dodecyl Maltoside | 0.07 |
| Water | q.s. to 100 |
| pH was adjusted to 6.5 | |

This formulation is effective in the treatment of allergic conjunctivitis.

EXAMPLE 12

The following anti-inflammatory formulation was prepared:

| | % (w/v) |
|---|---|
| $NaH_2PO_4$ | 0.18 |
| $Na_2HPO_4$ | 0.12 |
| Mannitol | 3.3 |
| BAC | 0.01 |
| EDTA | 0.01 |
| Dexamethasone Phosphate | 0.01 |
| Dodecyl maltoside | 0.07 |
| HPMC | 2.0 |
| Water | q.s to 100.0 |
| pH | 6.5 |

This formulation is effective in controlling inflammation in the eye.

We claim:

1. A method of enhancing the penetration of a drug across mucus covered epithelial tissues, which comprises:

topically applying to the mucus covered epithelial tissue a pharmaceutical composition comprising a therapeutically effective amount of the drug and an amount of a substituted glycoside effective to enhance penetration of the drug across the mucus covered epithelial tissue said substituted glycoside having the formula:

$$R_1-Z-(R_2)_x$$

wherein, $R_1$ is a hydrophobic group including saturated and unsaturated aliphatic hydrocarbon groups which range from 8 to 28 carbons in length with 1 to 5 double bonds and said aliphatic hydrocarbon group can be a straight or branched chain and may be substituted by one or more aromatic, cycloaliphatic or hydrophilic groups;

$R_2$ is a group derived from any cyclic or acyclic saccharide containing 4–7 carbons;

X is an integer from 1–10; and

Z is an oxy (—O—), carbonyloxy

phosphoryl

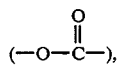

thio (—S—), or carboxamido

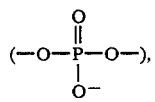

group where $R_2$ is covalently bound to such group.

2. The method of claim 1 wherein the substituted glycoside is selected from the group consisting of:

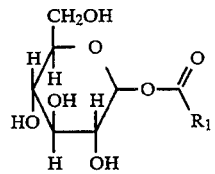 [A]

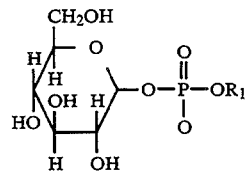 [B]

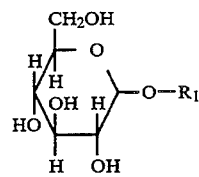 [C]

-continued

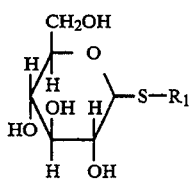

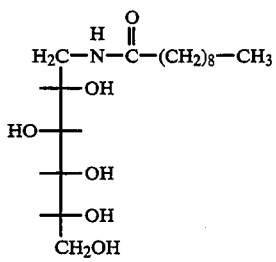

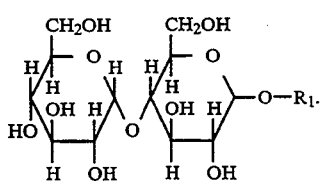

3. The method of claim 1 wherein the substituted glycoside is dodecyl maltoside.

4. The method of claim 1 wherein the substituted glycoside concentration is about 0.01–5 wt. %.

5. The method of claim 4 wherein the concentration is about 0.01–1.0 wt. %.

6. The method of claim 1 wherein the composition further comprises a viscosity enhancing polymer in an amount sufficient to provide the composition with a viscosity of up to about 1,000 centipoise.

7. The method of claim 6 wherein the composition comprises a viscosity enhancing polymer selected from the group consisting of: alginates, carrageenan, gar, karaya, locust beans, tragacanth, zanthan, carbomer, hydroxyethylcellulose, hydroxypropylcelluiose, hydroxypropylmethylcellulose, methylcellulose, polyvinyl alcohol, polyvinyl pyrrolidone, carboxymethylcellulose and agarose.

8. The method of claim 7 wherein the viscosity enhancing polymer comprises hydroxypropylmethylcellulose.

9. The method of claim 8 wherein the substituted glycoside is dodecyl maltoside.

10. The method of claim 9 where in the dodecyl maltoside is present at a concentration of about 0.01% to about 1.0% and the hydroxypropylmethylcellulose is present in an amount sufficient to provide the composition with a viscosity of between about 50 and 300 centipoise.

* * * * *